US00PP10955P

United States Patent [19]

Hoff

[11] Patent Number: Plant 10,955

[45] Date of Patent: Jun. 8, 1999

[54] LILY PLANT NAMED 'BLUE EYES'

[75] Inventor: Petrus Mattheus Maria Hoff, Steenbergen, Netherlands

[73] Assignee: Hoffgaarde B.V., Netherlands

[21] Appl. No.: 08/869,156

[22] Filed: Jun. 4, 1997

[51] Int. Cl.[6] ..... A01H 5/00

[52] U.S. Cl. ..... Plt./87.4

[58] Field of Search ..... Plt./87.4

[56] References Cited

U.S. PATENT DOCUMENTS

P.P. 5,959 4/1987 McRae ..... Plt./87.4

OTHER PUBLICATIONS

GTITM UPOVROM Citation for 'Blue Eyes' as per NZ PBR LIL 035; Jul. 14, 1997.

*Primary Examiner*—Howard J. Locker
*Assistant Examiner*—Kent L. Bell
*Attorney, Agent, or Firm*—Webb Ziesenheim Bruening Logsdon Orkin & Hanson, P.C.

[57] ABSTRACT

A new and distinct cultivar of lily plant named 'Blue Eyes', particularly characterized by large pinkish flowers having yellow on the middle of the tepals, height of about 150 cm, and dark green stem and leaves.

1 Drawing Sheet

BACKGROUND OF THE INVENTION

The present invention comprises a new and distinct cultivar of Asiatic of the Genus lily Lilium, and hereinafter referred to by the cultivar name 'Blue Eyes'.

The new cultivar is a product of a planned breeding program which had the objectives of creating new lily cultivars with the capacity to produce stems and flowers for cut-flower production.

The new cultivar was originated from a hybridization made by the inventor Messr. Petrus Mattheus Maria Hoff in a controlled breeding program at Hoffgaarde B.V., Franseweg 9, NL-4651 PV Steenbergen, The Netherlands, in 1992. The purpose of the breeding program was to obtain a tall variety having a large flower. The female and male parents were seedlings originated by Hoffgaarde B.V. which were proprietary and maintained by Hoffgaarde B.V. for breeding purposes.

The new cultivar was discovered and selected as one flowering plant within the progeny of the stated cross by the inventor in a controlled environment in Steenbergen, The Netherlands.

The first act of asexual reproduction using bulbs and bulb components of the new cultivar was accomplished by the inventor in 1994 in a controlled environment in Steenbergen, The Netherlands.

Horticultural examination of clonal specimens has demonstrated that the combination of characteristics as herein disclosed for the new cultivar are firmly fixed and are retained through successive generations of asexual reproduction.

The new cultivar has not been observed under all possible environmental conditions. The phenotype may vary with variations in environment, such as temperature, light, intensity, and day length. The following observations, measurements and comparisons describe plants grown in Steenbergen, The Netherlands, under greenhouse conditions which approximate those generally used in commercial practice.

The following traits have been repeatedly observed and are determined to be basic characteristics of the new cultivar which, in combination, distinguish this lily as a new and distinct cultivar.

1) Pinkish flowers suffusing to white and yellow towards the central and basal portions of the tepals.

2) Plant height of 150 cm.

3) Large flowers.

DESCRIPTION OF THE DRAWING

The accompanying color photographic drawing shows typical flower characteristics of the new cultivar, with colors being as true as possible with illustrations of this type.

DESCRIPTION OF THE NEW PLANT

In the following description, color references are made to The Royal Horticultural Society Colour Chart. The color values were determined at Steenbergen, The Netherlands.

THE PLANT

Classification:

*Botanic.*—Lilium.

*Commercial.*—Hybrid asiatic lily for cut-flower production named 'Blue Eyes'.

Form:

*Height.*—About 150 cm.

*Growth habit.*—Upright, erect, strong and vigorous.

Stem:

*Diameter.*—1 cm average.

*Color.*—Dark green with a tinge of anthocyanin.

Foliage:

*Quantity.*—Normal amount for varieties of this market class.

*Size of leaf.*—About 12 cm long; about 0.9 cm wide.

*Shape of leaf.*—Elliptic.

*Margin of leaf.*—Entire.

*Apex of leaf.*—Acute to acuminate.

*Base of leaf.*—Cordate.

*Arrangement of leaf.*—Sessile.

*Texture of leaf.*—Smooth.

*Aspect.*—Shiny.

*Color.*—Upper side: Dark green with weak to medium glossiness. Lower side: Dark green.

Bulbs:

*Size.*—12–14 cm in circumference.

*Color.*—Pink-red, fading into white.

THE BUD

Shape: Obovate.
Size: 14 cm in length.
Peduncle:
*Character.*—Erect.
*Color.*—Green with a tinge of anthocyanin.

THE FLOWER

Blooming habit: 120 days after planting.
Lastingness of the bloom: 10–15 days.
Size: 15 cm in diameter.
Borne: Umbellate, 3 flowers per umbel.
Nectary color: Green fading to red-purple.
Tepalage:
*Number of tepals.*—6.
*Tepal shape.*—Obovate.
*Arrangement.*—Hexagonal.
*Color.*—Red Group 54C on the tip and to the left and right sides of the tepals, suffusing to white and Yellow Group 10B towards the central and basal portions of the tepal's upper surface. Under surface coloration is similar to the upper surface but is more dull.
*Spotting.*—Present on inner and outer tepals; Red-purple in color, darker than the main coloration of the upper surface on the tepals. Typical of other varieties in this market class.
*Size.*—Inner tepals: About 11 cm in length and 5 cm in width. Outer tepals: About 11 cm in length and 3.5 cm in width.
*Aspect.*—Shiny.
*Texture.*—Smooth.
Pedicel:
*Length.*—10 cm.
*Character.*—Upright.
*Color.*—Dark green.
Disease resistance: No problems have been observed.
Fragrance: None.
Lasting quality: Good.

REPRODUCTIVE ORGANS

Stamens:
*Number.*—6.
*Length.*—7 cm.
*Anther color.*—Brown-yellow.
*Pollen color.*—Orange.
Pistils:
*Number.*—1.
*Stigma.*—Purple, located above the anthers.
*Style length.*—About 6 cm.
*Ovary color.*—Green.
*Fruit color at maturity.*—Pink-green.
*Fruit size.*—About 1.5 cm in length and 0.4 cm in width.

I claim:

1. A new and distinct variety of lily plant substantially as shown and described.

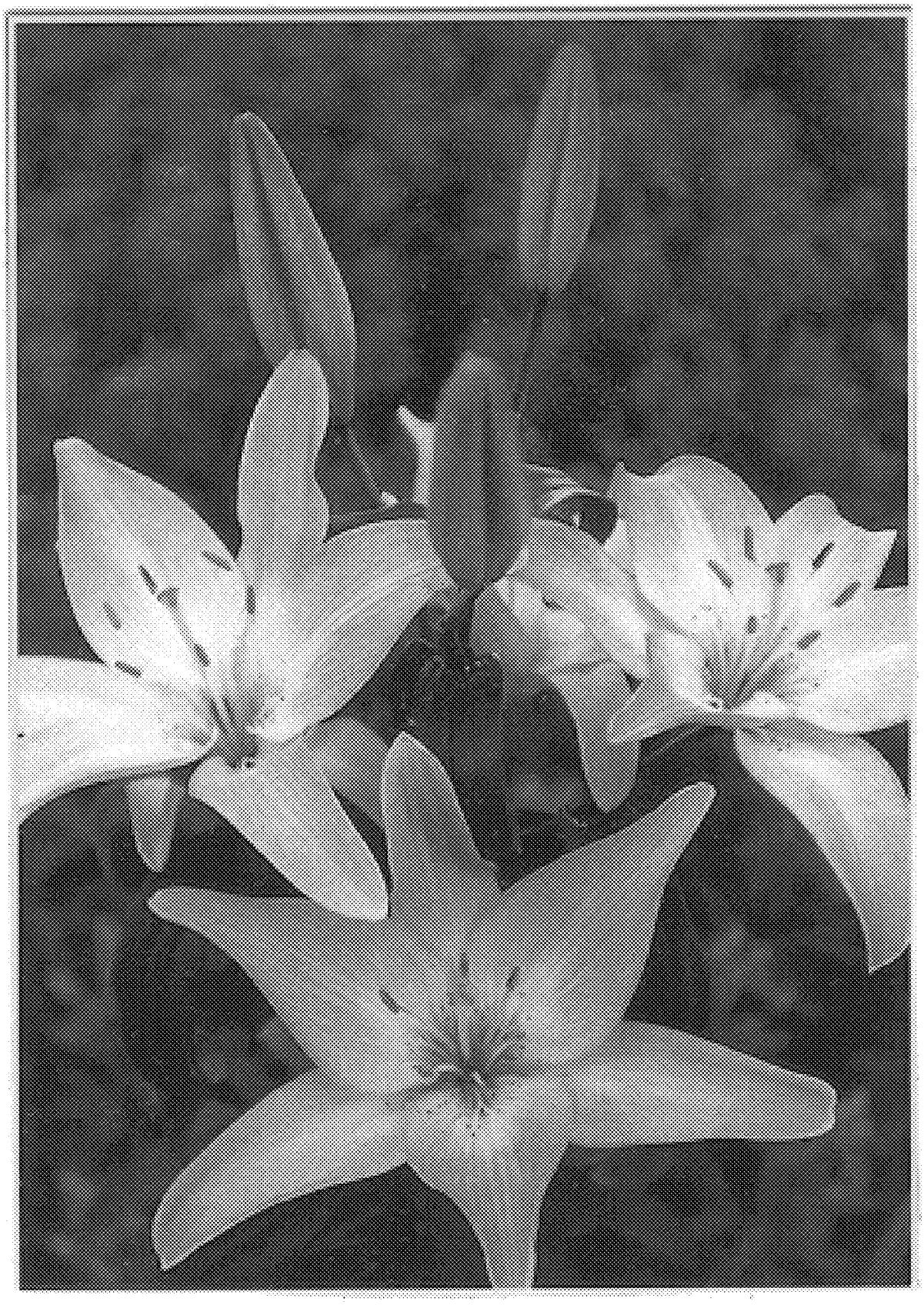

* * * * *